United States Patent [19]

Khan et al.

[11] Patent Number: 5,116,623

[45] Date of Patent: May 26, 1992

[54] PERIODATE IODOPHOR COMPOSITION WITH INCREASED STABILITY

[75] Inventors: Mohammad A. Khan, Sandy; John F. Moellmer, Salt Lake City, both of Utah

[73] Assignee: Becton-Dickinson and Company, Franklin Lakes, N.J.

[21] Appl. No.: 643,737

[22] Filed: Jan. 22, 1991

[51] Int. Cl.$^5$ ............................................. A61K 33/18
[52] U.S. Cl. ................................... 424/616; 424/613; 424/667; 424/668
[58] Field of Search .................. 424/78, 80, 667, 668, 424/669, 613, 616

[56] References Cited

U.S. PATENT DOCUMENTS

| | | | |
|---|---|---|---|
| 1,280,580 | 10/1918 | Swett | 167/90 |
| 1,925,135 | 9/1933 | Chandler | 167/70 |
| 1,964,518 | 6/1934 | Karns | 167/17 |
| 2,386,252 | 10/1945 | Mendelsohn | 167/17 |
| 2,918,400 | 12/1959 | Loonam | 167/17 |
| 2,987,505 | 6/1961 | Werner | 260/77.5 |
| 3,028,299 | 4/1962 | Winicov et al. | 167/17 |
| 3,274,116 | 9/1966 | Mills | 252/106 |
| 3,282,777 | 11/1966 | Ceriotti | 167/43 |
| 3,288,708 | 11/1966 | Cordle et al. | 210/62 |
| 3,644,650 | 2/1972 | Sabatelli et al. | 424/341 |
| 4,113,857 | 9/1978 | Shetty | 424/150 |
| 4,271,149 | 6/1981 | Winicov et al. | 424/341 |
| 4,427,631 | 1/1984 | Bunting et al. | 522/133 |

FOREIGN PATENT DOCUMENTS 993319  9/1961  United Kingdom .

OTHER PUBLICATIONS

D. R. Clippinger, C. W. Foulk, Electrometric Indicators with the Dead-Stop End-Point System, Apr., 1989, pp. 216-218.

Primary Examiner—Thurman N. Page
Assistant Examiner—Peter F. Kulkosky
Attorney, Agent, or Firm—Hoffmann & Baron

[57] ABSTRACT

A germicidal iodophor composition is disclosed having improved long term stability, by controlling the pH of the composition and supplementing the elemental iodine with a source of periodate. The present invention comprises an iodophor composition comprising periodate and having a pH of about 4.5 or below. Processes for making the iodophors, as well as methods for killing bacteria on a substrate using these germicidal iodophor compositions are also disclosed.

10 Claims, No Drawings

PERIODATE IODOPHOR COMPOSITION WITH INCREASED STABILITY

The present invention is directed to an iodophor and, more particularly, to a method of making an iodophor composition and the resulting iodophor composition which comprises periodate. Iodophor compositions of the present invention exhibit long term stability even when subjected to gamma radiation.

BACKGROUND OF THE INVENTION

Iodophor compositions useful as bactericides, such as surgical hand-scrubbing solutions, have been previously disclosed. Iodine has been widely used in the past for bactericides since elemental iodine is very effective in killing a wide variety of germs and bacteria. Some known iodophor germicidal compositions have lacked adequate stability since normal aging converts elemental iodine into iodide ions thereby causing a loss of efficacy. Due to this natural tendency of elemental iodine to dissociate into iodide ions, it has been suggested to add oxidizing agents to the germicidal composition in order to reconvert the iodide ions into elemental iodine.

The present invention provides improved stability in comparison to known germicidal iodophor compositions.

SUMMARY OF THE INVENTION

The present invention provides long term stability to a germicidal iodophor composition, even when subjected to gamma radiation, by controlling the pH of the composition and supplementing the elemental iodine with a source of periodate. The present invention comprises a germicidal iodophor composition comprising periodate and having a pH of about 4.5 or below, as well as processes for making and methods for using the iodophor.

DETAILED DESCRIPTION

According to one embodiment of the present invention, an aqueous iodophor composition is prepared such that the amount of elemental iodine ($I_2$) is maintained at a level of about 0.5%–1.25% by weight. Unless otherwise noted, all percentages herein are on a weight basis. According to this embodiment of the present invention, the initial germicidal iodophor composition comprises about 60 to 90% water, about 2 to 6% surfactant, about 3 to 14% detergent, about 0.5 to 1.25% elemental iodine, about 0.01 to 0.1% hydrogen peroxide and about 0.01 to 0.3% of a source of periodate. An organic iodine complexing agent in the range of 5 to 20%, such as polyvinyl pyrrolidone, polyoxypropylene polyoxyethylene condensates, alkylaryl sulfonates, and primary alcohol ethoxylates, may also be added for particular applications or to facilitate the preparation of this composition. The source of periodate may be selected from inorganic compounds that include, but are not limited to, sodium and potassium periodates.

Hydrogen peroxide is useful for oxidizing any reducing agent present as impurities and tends to increase the stability of the formulation. The germicidal composition of the present invention is particularly suited for use as a topical skin disinfectant such as a surgical hand scrub, a personnel hand wash and a patient pre-operative prepping agent. It may also be used as an antiviral agent and as an antiseptic agent for any external applications.

Suitable surfactants for use in the iodophors of the present invention include alkyl phenol ethoxylates, primary alcohol ethoxylates, PEG lanolin ethoxylates and polyoxypropylene-polyoxyethylene condensates. The detergent utilized in a preferred embodiment of the present invention comprises ammonium nonoxynol-A sulfate, however other suitable detergents include sulfated alkyl phenol ethoxylates, alkylaryl sulfonates, primary alkyl sulfates and phosphated detergents.

The present invention utilizes periodate in order to improve the stability of the elemental iodine over extended periods of time and, also, when the iodophor composition is subjected to gamma radiation. Since periodate contains four oxygen atoms it is a strong oxidizing agent, generating four moles of iodine per mole of periodate. Periodates react with iodide according to the following reaction:

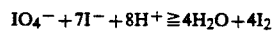

$$IO_4^- + 7I^- + 8H^+ \geqq 4H_2O + 4I_2$$

Since normal aging, as well as exposure to radiation, converts the germicidally-effective iodine in the iodophor to iodide causing a loss of efficacy, the presence of periodate which reconverts the iodide to iodine brings back efficacy and thus results in a longer shelf-life.

While the pH of the iodophor of the present invention is preferably maintained at a level of about 4 or below, one preferred embodiment of the present invention is maintained at a pH of 3–4. By maintaining the pH above 3, the tendency for the composition to cause staining and irritation which could result from higher acidity conditions will be reduced.

Iodophors of the present invention are preferably prepared by mixing together the sources of elemental iodine, iodide and periodate, surfactants, detergents and water. Finally the pH is adjusted to the desired value. Although these solutions are considered to be self sterilizing, microbial contamination of iodophors has been reported. Iodophors used by hospital professionals must be free of microbial contamination for infection control. It is, therefore, desirable to have iodophors irradiated so as to have sterile products for use in a hospital environment.

In order to illustrate the differences in efficacy between the iodophor compositions of the present invention which comprise, periodate and an iodophor composition containing iodate, the following test was performed:

One preferred embodiment of the present invention is an iodophor composition having a germicidally effective amount of elemental iodine in a range of about 0.8 to 1.2%, about 0.2% periodate, a pH of about 4, and whereby the initial composition is subjected to gamma radiation in doses of about 1.5–4.0 Mrads, preferably about 2.0–3.5 Mrads and most preferably about 2–3 Mrads.

The iodophor compositions of the present invention are particularly suitable for use as hand scrubs by medical professionals prior to surgery. The iodophor compositions of the present invention advantageously kill germs upon contact and are therefore also useful as an agent for cleaning wounds, a preoperative patient prepping agent, a personnel handwash, and a topical disinfecting agents for external applications.

The present invention therefore comprises a method of killing bacteria or germs by contacting a substrate harboring germs or bacteria with an iodophor composition of the present invention.

EXAMPLE

Four-ounce bottles were filled with one hundred milliliters of a non-stabilized iodophor surgical scrub solution. As used herein, the term "non-stabilized" is used to indicate that an oxidizing agent has not been added to convert iodide back to iodine. 0.2 grams of sodium iodate was added to half of the bottles and 0.2 grams of sodium periodate was added to the remaining bottles.

Samples were selectively irradiated with 2.5 Mrads of gamma radiation, aged under controlled temperature conditions at 22° C. and 52° C., and assayed to determine the percentage of elemental iodine. Samples were tested prior to sealing the bottles and at 5 weeks, 10 weeks, 15 weeks and 20 weeks. Those skilled in the art will appreciate that for testing purposes, increasing the storage temperature of the iodophor compositions has the same effect on the percentage of elemental iodine as longer storage periods at room temperature (22° C.).

Results

Table 1 shows that the percentage of iodine in the samples aged for 20 weeks at 52° C. and irradiated at 2.5 Mrads, was significantly higher in the samples stabilized with the periodate compared to those stabilized with iodate.

TABLE 1
DATA FROM IODATE/PERIODATE STUDY
(Percent Iodine)

| Sample | Week 0 | Week 5 | Week 10 | Week 15 | Week 20 |
|---|---|---|---|---|---|
| iodate non-irrad. room temp. | 1.22,1.23, 1.23,1.23, 1.23 | 1.25,1.24, 1.24,1.25, 1.24 | 1.29,1.27, 1.28,1.26, 1.25 | 1.24,1.24, 1.27,1.22, 1.26 | 1.25,1.23, 1.25,1.21, 1.22 |
| periodate non-irrad. room temp. | 1.25,1.25, 1.26,1.26, 1.25 | 1.25,1.25, 1.26,1.26, 1.28 | 1.29,1.29, 1.29,1.28, 1.31 | 1.25,1.26, 1.27,1.28, 1.26 | 1.22,1.22, 1.23,1.24, 1.24 |
| iodate irradiated room temp. | 1.23,1.23, 1.23,1.23, 1.23 | 1.24,1.23, 1.24,1.24, 1.24 | 1.26,1.26, 1.25,1.25, 1.29 | 1.25,1.25, 1.26,1.24, 1.25 | 1.24,1.23, 1.25,1.22, 1.23 |
| periodate irradiated room temp. | 1.23,1.22, 1.24,1.24, 1.23 | 1.25,1.24, 1.25,1.25, 1.24 | 1.26,1.27, 1.27,1.27, 1.28 | 1.25,1.24 1.29,1.27, 1.30 | 1.25,1.25, 1.25,1.24, 1.25 |
| iodate non-irrad. 52 deg C. | 1.23,1.24, 1.23,1.23, 1.23 | 1.25,1.26, 1.27,1.28, 1.27 | 1.20,1.21, 1.22,1.20, 1.22 | 1.18,1.20, 1.17,1.17, 1.17 | 1.13,1.14, 1.12,1.12, 1.12 |
| periodate non-irrad. 52 deg C. | 1.25,1.28, 1.25,1.25, 1.24 | 1.28,1.27, 1.28,1.28, 1.29 | 1.23,1.20, 1.21,1.22, 1.21 | 1.15,1.17, 1.17,1.17, 1.16 | 1.12,1.13, 1.13,1.13, 1.12 |
| iodate irradiated 52 deg C. | 1.23,1.23, 1.22,1.23, 1.23 | 1.09,1.09, 1.09,1.08, 1.09 | 1.04,1.03, 1.00,1.03, 1.06 | 0.91,0.94, 0.92,0.91, 0.93 | 0.79,0.81, 0.79,0.78, 0.80 |
| periodate irradiated 52 deg C. | 1.25,1.24, 1.24,1.25, 1.24 | 1.13,1.12, 1.14,1.12, 1.13 | 1.07,1.07, 1.06,1.08, 1.10 | 0.99,0.99, 1.01,1.02, 0.98 | 0.91,0.92, 0.92,0.94, 0.91 |

Table 2 indicates the average percentage of elemental iodine of the five measurements indicated in Table 1.

TABLE 2
DATA FROM IODATE/PERIODATE STUDY
(Percent iodine)

| | Week 0 | Week 5 | Week 10 | Week 15 | Week 20 |
|---|---|---|---|---|---|
| iodate non-irrad. room temp. | 1.23 | 1.24 | 1.27 | 1.25 | 1.23 |
| periodate non-irrad. room temp. | 1.25 | 1.26 | 1.29 | 1.26 | 1.23 |
| iodate irradiated room temp. | 1.23 | 1.24 | 1.26 | 1.25 | 1.23 |
| periodate irradiated room temp. | 1.23 | 1.25 | 1.27 | 1.27 | 1.25 |
| iodate non-irrad. 52 deg C. | 1.23 | 1.27 | 1.21 | 1.18 | 1.13 |
| periodate non-irrad. 52 deg C. | 1.25 | 1.28 | 1.21 | 1.16 | 1.13 |
| iodate irradiated 52 deg C. | 1.23 | 1.09 | 1.03 | 0.92 | 0.79 |
| periodate irradiated 52 deg C. | 1.24 | 1.13 | 1.08 | 1.00 | 0.92 |

What is claimed is:

1. An aqueous iodophor composition comprising:
   elemental iodine in a germicidally effective amount of about 0.5–1.25%;
   about 0.01–0.3% of periodate which maintains the level of elemental iodine by oxidation;
   said composition having a pH of below about 4.5;
   wherein said elemental iodine is maintained at a level of about 0.5%–1.25% by weight and wherein the percentage of iodine in the composition aged for 20 weeks at 52° C. and irradiated at 2.5 Mrads is higher than in the same composition not containing periodate.

2. An iodophor composition according to claim 1 wherein said pH is about 3–4.

3. An iodophor composition according to claim 1 wherein said composition comprises about 0.1–0.3% periodate.

4. An iodophor composition according to claim 1 comprising at least 1.1% elemental iodine, about 0.15–0.25% periodate, and a pH of up to 4.0.

5. An iodophor composition according to claim 4 further comprising a detergent and a surfactant.

6. A process for preparing an aqueous iodophor comprising the steps of:
   mixing water with a source of elemental iodine sufficient to establish a level of elemental iodine of about 0.5–1.25%;
   adding about 0.01–0.3% periodate to said mixture;
   adjusting the pH of said composition to about 4.5 or below;
   wherein said elemental iodine is maintained at a level of about 0.5%–1.25% by weight and wherein the percentage of iodine in the composition aged for 20 weeks at 52° C. and irradiated at 2.5 Mrads is higher than in the same composition not containing periodate.

7. A process according to claim 6 wherein said periodate is added in the amount of about 0.15–0.25% by weight and said pH is adjusted to about 3–4.

8. A process according to claim 6 further comprising the step of irradiating said iodophor with gamma radiation.

9. A process according to claim 8 wherein said iodophor is irradiated with 1.5–4.0 Mrads of gamma radiation.

10. A process according to claim 8 further comprising the steps of adding at least one detergent, adding at least one surfactant, and adding hydrogen peroxide to said iodophor.

* * * * *